US007127959B2

(12) United States Patent
Blum et al.

(10) Patent No.: US 7,127,959 B2
(45) Date of Patent: Oct. 31, 2006

(54) PROCESS FOR ASSESSING INHIBITION OF PETROLEUM CORROSION

(75) Inventors: Saul C. Blum, Monroe, NJ (US); Guido Sartori, Milan (IT); Winston K. Robbins, New Providence, NJ (US); Liza Monette, Houston, TX (US); Andreas Vogel, Steinfeld (DE); Mohsen S. Yeganeh, Piscataway, NJ (US)

(73) Assignee: ExxonMobil Research and Engineering Company, Annandale, NJ (US)

( * ) Notice: Subject to any disclaimer, the term of this patent is extended or adjusted under 35 U.S.C. 154(b) by 0 days.

(21) Appl. No.: 11/255,362

(22) Filed: Oct. 21, 2005

(65) Prior Publication Data
US 2006/0037414 A1  Feb. 23, 2006

Related U.S. Application Data

(63) Continuation of application No. 10/675,730, filed on Sep. 3, 2003, now abandoned.

(60) Provisional application No. 60/424,788, filed on Nov. 8, 2002.

(51) Int. Cl.
*G01N 17/00* (2006.01)
(52) U.S. Cl. ............................ 73/865.6; 73/86; 422/53
(58) Field of Classification Search ................ 73/865.6, 73/86; 422/53
See application file for complete search history.

(56) References Cited

U.S. PATENT DOCUMENTS

| 3,014,864 | A | * | 12/1961 | Hughes et al. ............... 507/243 |
| 3,017,356 | A | * | 1/1962 | Hughes et al. ............... 507/242 |
| 3,018,246 | A | * | 1/1962 | Hughes et al. ............... 507/242 |
| 3,029,125 | A | * | 4/1962 | Hummel ........................ 422/16 |
| 3,079,220 | A | * | 2/1963 | Boies et al. ................... 422/19 |
| 3,131,029 | A | * | 4/1964 | Dieman ......................... 422/53 |
| 3,364,000 | A | * | 1/1968 | Stromberg .................... 44/391 |
| 3,639,876 | A | * | 2/1972 | Wilson ........................... 338/13 |
| 3,934,646 | A | * | 1/1976 | Robertson et al. ...... 165/104.21 |
| 3,957,440 | A | * | 5/1976 | Aussieker ..................... 422/53 |
| 3,960,496 | A | * | 6/1976 | Schieber ....................... 422/53 |
| 4,282,181 | A | * | 8/1981 | Pierce .......................... 422/53 |
| 4,335,072 | A | * | 6/1982 | Barnett et al. ................ 422/53 |
| 4,357,149 | A | * | 11/1982 | West et al. ................... 44/304 |
| 4,552,722 | A | * | 11/1985 | Fritscher et al. .............. 422/53 |
| 4,599,217 | A | * | 7/1986 | Winston et al. ............... 422/53 |
| 4,640,233 | A | * | 2/1987 | Draper et al. ............... 122/488 |
| 4,944,917 | A | * | 7/1990 | Madden et al. ............... 422/13 |
| 4,996,038 | A | * | 2/1991 | McAlister et al. ........... 423/522 |
| 5,254,310 | A | * | 10/1993 | Bressan ........................ 422/53 |

(Continued)

OTHER PUBLICATIONS

"Naphthenic Acid Corrosion Review", http://www.setlaboratories.com/nac.htm, Last modified Feb. 10, 2002.*

(Continued)

*Primary Examiner*—Hezron Williams
*Assistant Examiner*—Rodney Frank
(74) *Attorney, Agent, or Firm*—Ronald D. Hantman

(57) ABSTRACT

The present invention is an apparatus for simulating corrosion activity in liquid and vapor/condensate corrosion environments. The apparatus includes a container, including a lower region containing the liquid and an upper region, including a condenser, a heater for providing heat to the lower region such that the liquid is maintained at a given temperature, a vacuum pump for providing a partial vacuum at a given pressure in the upper region of the container, one corrosion probe removably positioned in the liquid, and a second corrosion probe removably positioned above the liquid.

9 Claims, 5 Drawing Sheets

U.S. PATENT DOCUMENTS

| | | | |
|---|---|---|---|
| 5,425,267 A * | 6/1995 | Herrmann et al. | 73/86 |
| 5,503,006 A * | 4/1996 | Babaian-Kibala et al. | 73/86 |
| 5,611,911 A * | 3/1997 | Edmondson | 208/47 |
| 5,630,964 A * | 5/1997 | Babaian-Kibala et al. | 252/389.23 |
| 5,714,664 A * | 2/1998 | Fearnside et al. | 208/184 |
| 5,965,785 A * | 10/1999 | Braden et al. | 208/184 |
| 6,677,765 B1 * | 1/2004 | Breen et al. | 324/691 |
| 6,679,987 B1 * | 1/2004 | Blum et al. | 208/263 |

OTHER PUBLICATIONS

"Corrosion Tests of 316L and Hastelloy in Simulated Tank Waste Solutions", Feb. 2000, http://www.pnl.gov/rpp-wtp/documents/BNFL-RPT-019.PDF.*

* cited by examiner

PROCESS FOR ASSESSING INHIBITION OF PETROLEUM CORROSION

This application claims the benefit of U.S. Provisional application 60/424,788 filed Nov. 8, 2002 and is a continuation of U.S. Pat. application No. 10/675,730 filed Sep. 3, 2003, now abandoned.

BACKGROUND OF THE INVENTION

The present invention relates to an apparatus for determining corrosion activity in a liquid and vapor/condensate corrosion environment. In particular, the corrosive environment is the interior of an oil refinery apparatus such as a pipestill.

Two leading causes of crude oil corrosion on metal surfaces in refinery pipestills are reactive sulfur compounds and naphthenic acids exposed to pipestill (400–800° F.) temperatures. Corrosion mitigation is practiced by dilution with non-corrosive crudes, installation of corrosion-resistant metallurgy, or addition of chemical corrosion inhibitors, either alone or in combination. Reactive sulfur corrosion e.g. from hydrogen sulfide, is recognized as occurring in either the liquid or vapor phase. On the other hand, naphthenic acid corrosion occurs in liquid and in condensate phases, is enhanced in high velocity regions, but is not believed to be a vapor phase phenomenon.

Commercial inhibitors are typically high boiling and, therefore, concentrate in the bulk liquid phase to minimize the risk of distillate contamination. However, multiple injection ports are frequently necessary to ensure that condensation zones in pipestills are contacted by these agents. This adds to the complexity and cost of inhibitor treatment while increasing the risk of contamination to the petroleum distillate streams. The ability to select a chemical agent that can provide metal protection in multi-phase regions with a single injection would make for a more effective treatment while overcoming the cost and potential product quality issues resulting from inhibitor applications at multiple locations.

Efforts to predict pipestill corrosion have primarily been based on corrosion test results, typically carried out in autoclaves. This can provide a measure of metal coupon corrosion in contact with a bulk liquid phase. However, a coupon placed above the liquid is in a fairly static vapor-liquid environment under pressure from enclosed autoclave. This is totally unlike the dynamic vapor-liquid conditions in pipestills, especially under vacuum in vacuum pipestills. Thus, autoclave corrosion tests are not reliable indicators of condensate phase corrosion and therefore inhibitor performance in that phase cannot be properly evaluated.

As a consequence, refineries using corrosion inhibitors monitor the impact on pipestills by insertion of invariably unreliable corrosion probes and by frequent inspections for evidence of corrosion. When the latter is suspected and/or detected, the refiner typically has three options. One is to add more corrosion inhibitor injection points at indicated locations; another is to alloy up those regions, and the third is to lower the crude feed total acid number (TAN) levels. TAN is typically measured by ASTM method D-664 and is expressed in units of milligrams KOH/gram of oil. Oils with TAN values below 0.5 are generally regarded as non-corrosive, between 0.5 and 1.0 as moderately corrosive, and corrosive above 1.0.

SUMMARY OF THE INVENTION

The present invention is an apparatus for simulating corrosion activity in liquid and vapor/condensate corrosion environments. The apparatus is used for selecting the highest performance petroleum corrosion inhibitor candidates under simulated refinery pipestill conditions. The conditions involve concurrent measurement of corrosion rate in a petroleum liquid at elevated temperature and in a vapor/condensate phase at a higher atmospheric equivalent temperature (AET). This higher effective temperature is achieved by the system being under partial vacuum such that lower pressures translate to higher AET values as in a refinery pipestill. The criterion for inhibitor selection is its ability, when added to a petroleum liquid, to mitigate naphthenic acid corrosion on metal surfaces in both condensate and liquid phases.

Naphthenic acid corrosion is known to occur at elevated temperatures in bulk liquids and in localized regions in refinery pipestills where liquid condensation occurs, but is not believed to occur in the vapor phase. Commercial inhibitors are intended to be high boiling so as to concentrate in the bulk liquid phase without contaminating distillate sidestreams. Therefore, multiple injection ports are frequently required to ensure that condensation zones in pipestills are contacted by these agents. This adds to the complexity and cost of inhibitor treatment while risking an increase in its level of contamination to the petroleum streams. The ability to select a chemical agent that can provide metal protection in multi-phase regions with a single injection would make for a more effective treatment while overcoming the cost and product quality issues resulting from inhibitor applications at multiple locations.

The apparatus comprises a container including a lower region containing the liquid and an upper region including a condenser, a heater for providing heat to the lower region such that the liquid is maintained at a given temperature, a vacuum pump for providing a partial vacuum at a given pressure in the upper region of the container, one corrosion probe removably positioned in the liquid, and a second corrosion probe removably positioned above the liquid.

In a preferred embodiment, the container of the apparatus includes an insulated column and the lower region is a flash in open communication with the insulated column and the upper region is a condenser in open communication with the insulated column. The apparatus may further include a means for providing an inert gas to the interior of the container.

DESCRIPTION OF THE PREFERRED EMBODIMENTS

A liquid/condensate corrosion test (LCCT) was conceived and assembled to study naphthenic acid corrosion in the liquid and condensate phases. The test liquid, usually containing naphthenic acids, is refluxed at a specified temperature under partial vacuum such that the atmospheric equivalent temperature (AET) in the vapor phase is higher than the bulk liquid. The lower the pressure, the higher the AET as described in ASTM method D-2892, Annex A-8.3. One pre-weighed carbon steel test coupon is suspended in the bulk liquid and another is suspended about one inch above the liquid level. Under gentle liquid reflux, the latter corresponds to a location where rising vapors and condensed vapors meet, hence this condensate zone is at a higher AET compared to the bulk liquid. This is intended to simulate the environment in a petroleum vacuum pipestill where the bulk liquid is also at a lower AET than the vapor/condensate regions. After a specified time, the exposure is halted, the coupons are wiped clean and rinsed with solvents, dried and reweighed. From the weight changes, the corrosion rates expressed in mils per year (mpy) are calculated and compared as a function of TAN as measured by ASTM method D-664 in units of mg. KOH/gram of oil.

Two approaches were devised for testing a candidate corrosion inhibitor. One version involved adding this agent to the test liquid prior to the test and comparing the corrosion rates obtained in its presence vs. its absence. The second version involved initially preconditioning the coupons by exposing them to test liquids containing the inhibitor essentially in the absence of naphthenic acids and recording the dried coupon weights. These coupons were then re-exposed in a test liquid containing both naphthenic acid and inhibitor and the weight change converted to corrosion rates for comparison purposes. The second version also simulates refinery practices where commercial inhibitors were injected into pipestills when feeds having no or low acid contents are being processed to precondition the metal surfaces. Then higher acid feeds were processed while a maintenance dose of inhibitor was continuously added.

By combining these refinery simulations, it became possible to evaluate and compare corrosion inhibitor candidates. Moreover, this could be accomplished under realistic conditions that resembled commercial operations without requiring refinery pipestills for experimental purposes.

Apparatus and Test Procedure

Figure 1:
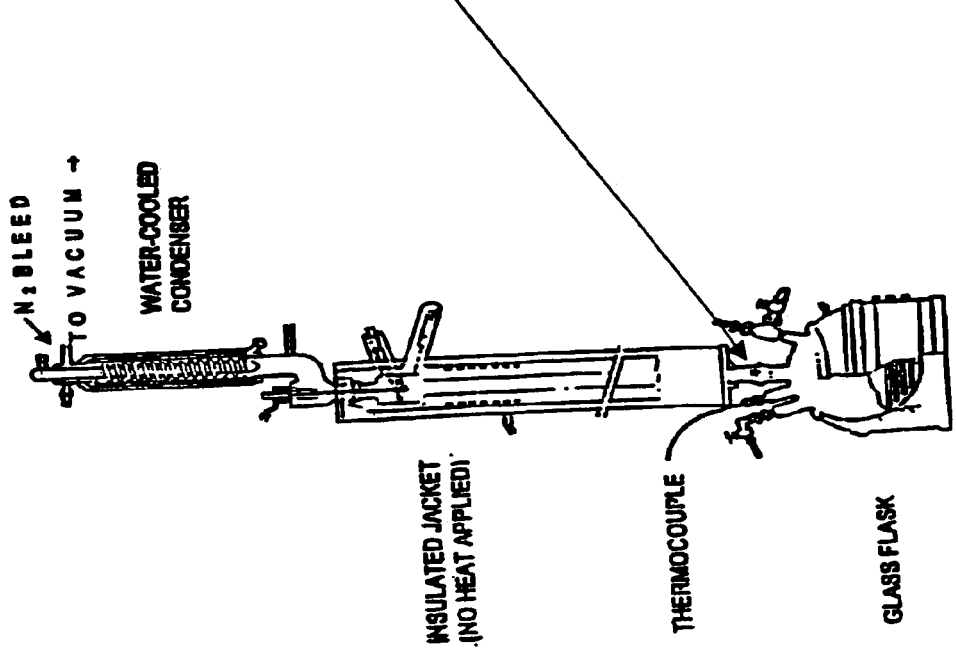
FIG. 1a shows a schematic diagram of the apparatus of the present invention.
FIG. 1b shows the test probe assembly.

The liquid/condensate corrosion test (LCCT) apparatus used is illustrated in FIG. 1a. A 250 ml distilling flask was attached to a 25 mm. column filled with stainless steel mesh packing. A water-cooled condenser was placed atop the condenser with provision for both vacuum and a nitrogen bleed. To the flask was added 110 grams of test liquid, a thermocouple, and a magnetic stirring bar. A test coupon assembly, shown in FIG. 1b, was suspended from a stainless steel wire from the bottom of the packed column such that the lower carbon steel coupon would be immersed in the liquid while the bottom edge of the upper coupon was about one inch above the liquid level. The test coupon assembly comprised a glass rod with multiple glass hooks. Carbon steel coupons were attached to the hooks as described above. The coupons were first cleaned sequentially with toluene, methylene chloride, and acetone, dried with nitrogen, and weighed. These coupons were made of 516–70 carbon steel, ¾"×½"×⅛" with an off-centered hole, ⅛" diameter, to permit hanging them on the glass hooks.

The apparatus was assembled and flushed with nitrogen to remove air. Vacuum was applied with a mechanical pump and regulated to the desired. pressure using a nitrogen bleed. The liquid was rapidly heated to temperature and stirred with a stirrer-heating mantle. A regulator was used to maintain the desired liquid/vapor temperature while the desired AET, set by the pressure. After maintaining these conditions for several hours, the flask was rapidly cooled by removal of the heat source. The coupons were removed, wiped with lint-free tissue, solvent rinsed as before, dried, and reweighed. From these weights, the corrosion rates, expressed as mils per year, were calculated.

EXAMPLE 1

Figure 2:
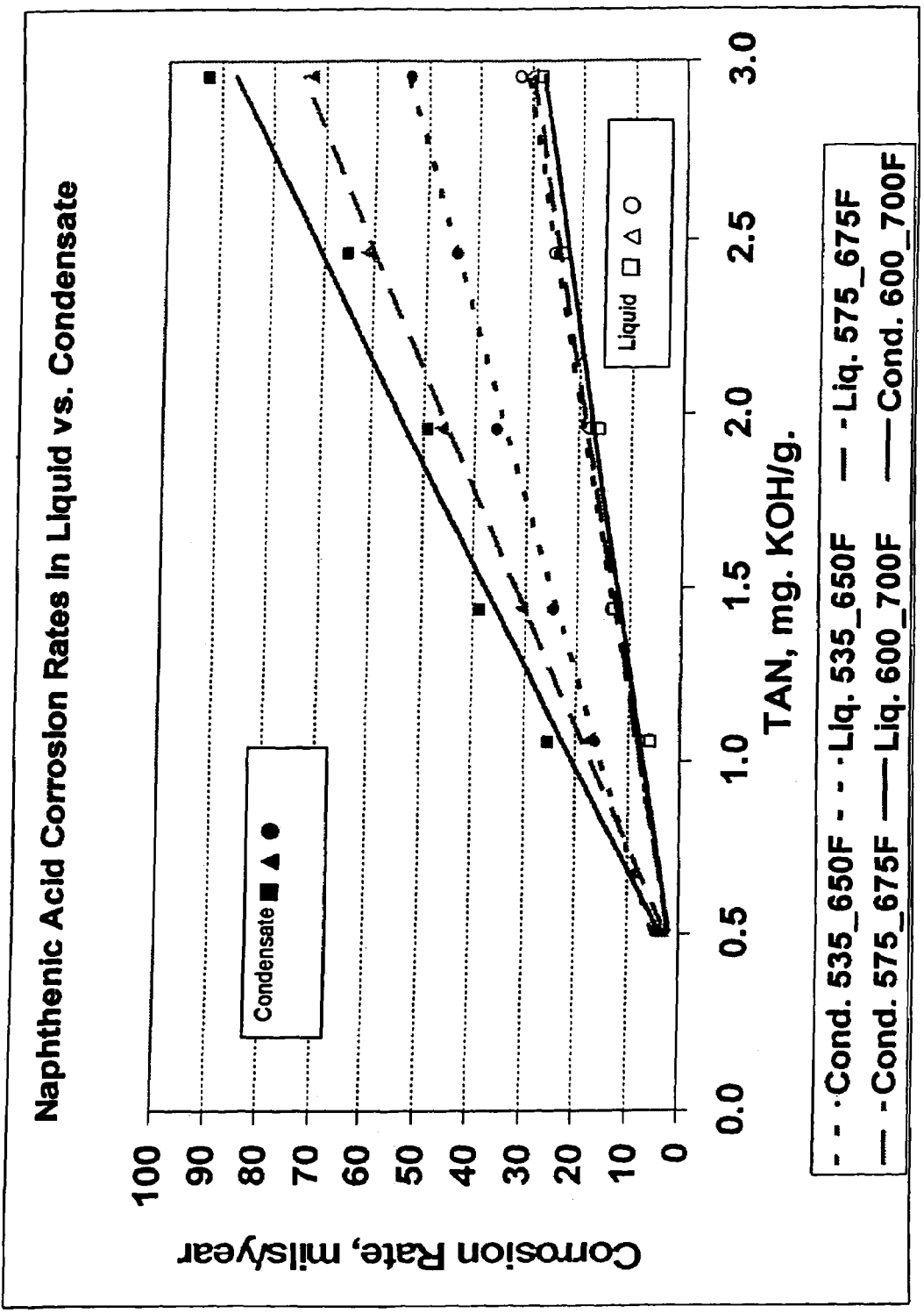
FIG. 2 shows corrosion rate versus solutions containing commercial naphthenic acids in a lube base oil.

The following series of experiments were used to demonstrate the ability to concurrently obtain corrosion rates in liquid and in condensate phases. A set of test solutions was prepared containing commercial naphthenic acids in a lube base oil having TAN values ranging from 0.5 to 3. Each solution was tested at three liquid temperatures 535, 575, and 600° F. and the vacuum adjusted so that the corresponding AET values were 600, 650, and 700° F., respectively. Coupons were exposed for 20 hours at test temperatures, the weight losses converted to corrosion rates in mils per year. These rates, plotted vs. TAN are shown in FIG. 2.

The results showed enhanced corrosion rates and, therefore, greater sensitivity in the condensate vs. the liquid. This is consistent with refinery pipestill environments where localized condensate corrosion is a particular concern and is believed to result from a localized naphthenic acid enrichment where vapor condensation occurs. These enhanced corrosion rates increased with AET and/or TAN while the rates in the liquid phase increased essentially due to TAN only.

EXAMPLE 2

Figure 3A:
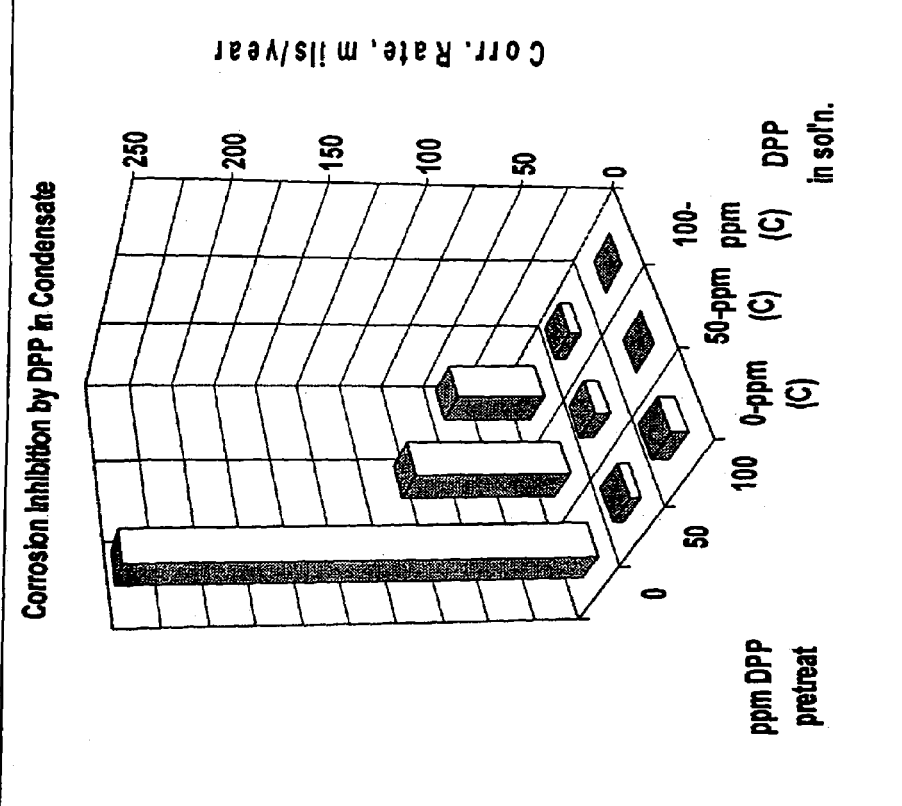
FIGS. 3a and 3b show the performance of diphenyl phosphate (DPP) as a corrosion inhibitor in a lube base oil having a TAN of 3 where carbon steel test coupons were exposed for 5 hours at 572° F. in the liquid and 662° F. atmospheric equivalent temperature in the vapor/condensate.
Figure 3B:
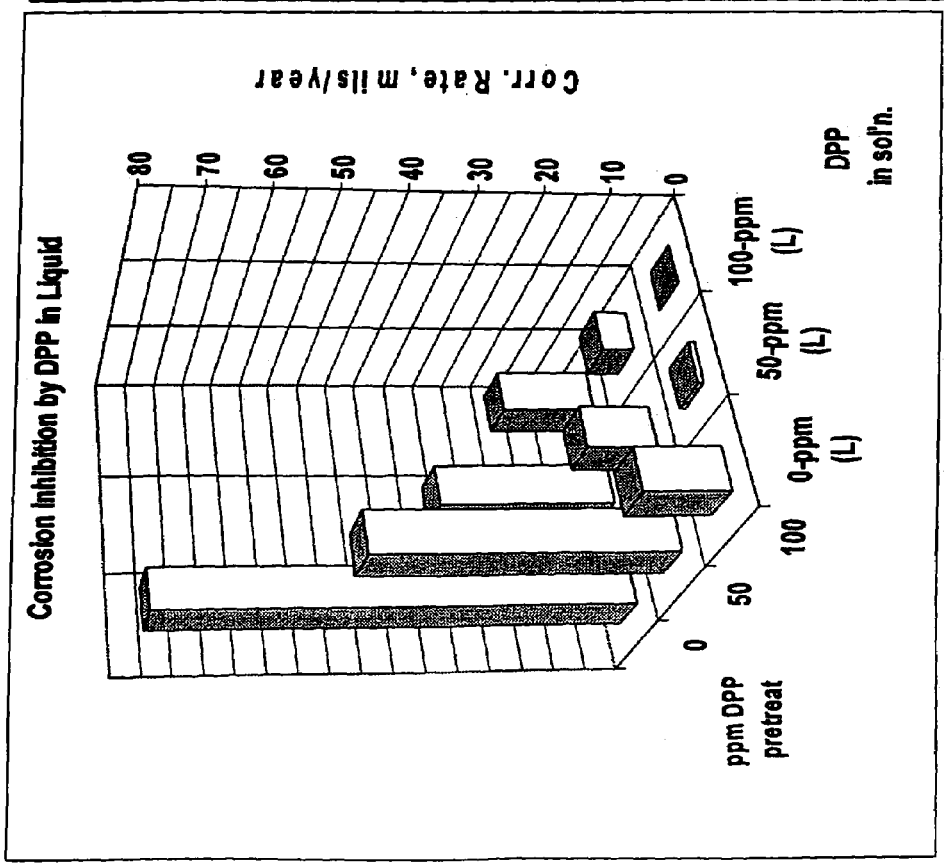

In this series of experiments, the performance of diphenyl phosphate (DPP) was evaluated as a corrosion inhibitor using the above-described methodology. Solutions of commercial naphthenic acids in a lube base oil having a TAN of 3 were subjected to the corrosion test for 5 hours at 572° F. liquid and 662° F. AET in the vapor/condensate. Up to 100 ppm of DPP was present in the solutions while some of the carbon steel coupons were pretreated with the lube oil containing up to 100 ppm DPP in the absence of acids before being exposed to the acidic test solution. FIGS. 3a and 3b present the matrix of corrosion rate test results of coupons exposed to the liquid and condensate phases, respectively.

EXAMPLE 3

Figure 4A:
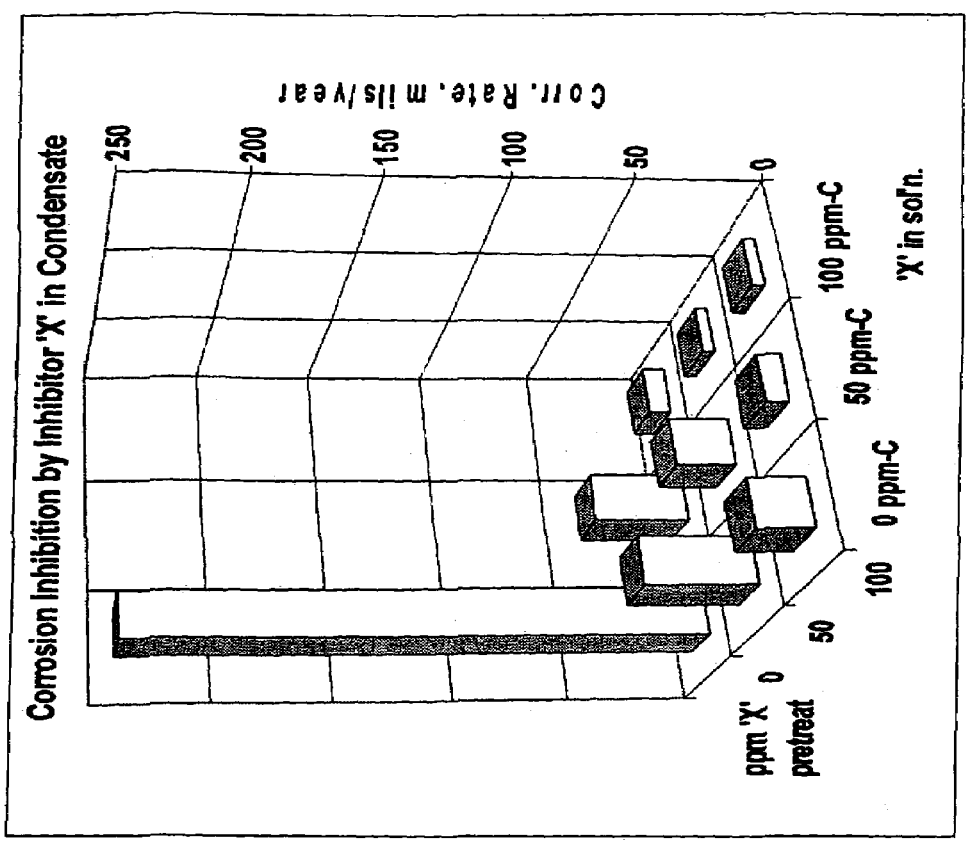
FIGS. 4a and 4b show the performance of a commercial inhibitor, "X" in a lube base oil having a TAN of 3 where carbon steel test coupons were exposed for 5 hours at 572° F. in the liquid and 662° F.
Figure 4B:
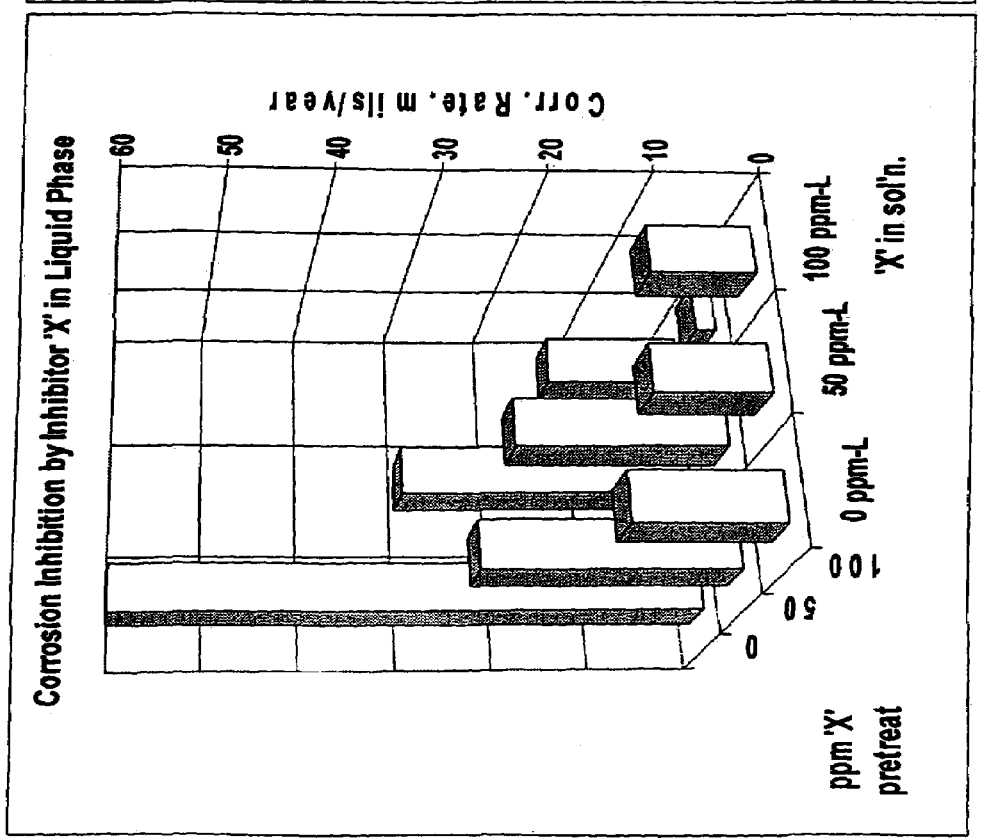

In this series of experiments, the performance of a commercial inhibitor, 'X', was evaluated using the same conditions as in Example 2. FIGS. 4a and 4b present the matrix of corrosion rate test results of coupons exposed to these liquid and condensate phases, respectively.

The results show substantial corrosion reduction in both liquid and condensate phases, especially when the coupons were pretreated with inhibitor 'X'. This example serves to demonstrate that the liquid: condensate corrosion test apparatus can assess the effectiveness of a commercial corrosion inhibitor formulation.

EXAMPLE 4

Figure 5B:
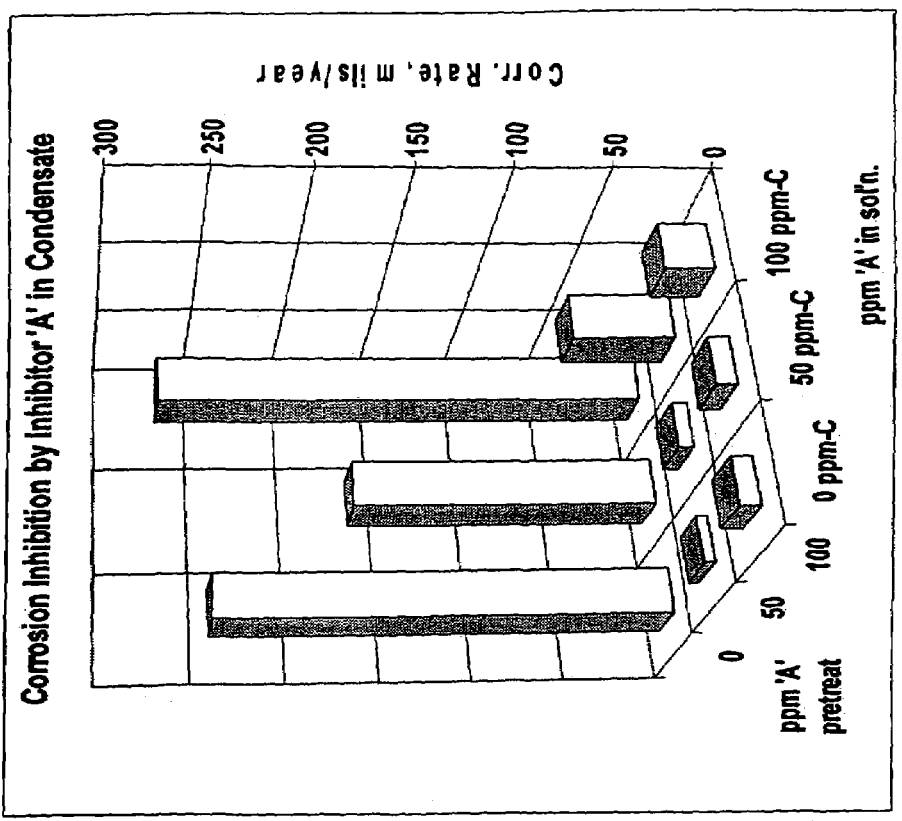
FIGS. 5a and 5b show the performance of a commercial inhibitor, "A" in a lube base oil having a TAN of 3 where carbon steel test coupons were exposed for 5 hours at 572° F. in the liquid and 662° F.
Figure 5A:
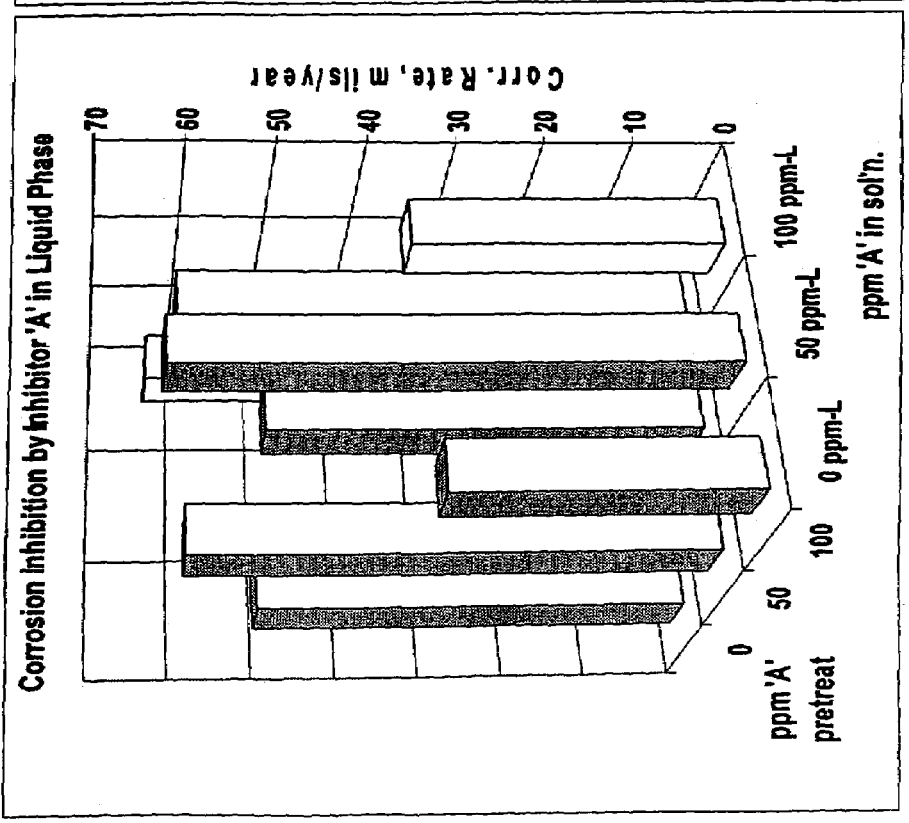

In this series of experiments, the performance of a commercial inhibitor, 'A', was evaluated using the same conditions as in Examples 2 and 3 and the results are presented for comparative purposes. FIGS. 5a and 5b present the matrix of corrosion rate test results of coupons exposed to these liquid and condensate phases, respectively.

These results only show substantial corrosion reduction in condensate phase and only when the test coupons were pretreated with inhibitor 'A'. However, it was ineffective in the liquid phase, even with prior coupon pretreatments. This example, compared with Example 3, further demonstrates this system's ability to discriminate among inhibitor effectiveness under simulated pipestill conditions.

What is claimed is:

1. An apparatus for simulating corrosion activity due to reactive sulfur compounds and/or naphthenic acid in a refinery process unit having a liquid and vapor/condensate corrosion petroleum enviromnent comprising:
    a) a container, including a lower region containing a liquid including said reactive sulfur compounds and/or naphthenic acid to simulate a refinery process unit liquid corrosion petroleum environment, and an upper region, including a condenser to simulate a refinery process unit vapor/condensate corrosion petroleum environment,
    b) a heater for providing heat to said lower region such that said liquid is maintained at a given temperature,
    c) a vacuum pump for providing a partial vacuum at a given pressure in said upper region of said container,
    d) one corrosion probe removably positioned in said liquid entirely in said liquid corrosion petroleum environment, and
    e) a second corrosion probe removably positioned entirely above said liquid in said vapor/condensate corrosion petroleum environment.

2. The apparatus of claim 1 wherein said container includes an insulated column and said lower region is a flask in open communication with said insulated column and said upper region is a condenser in open communication with said insulated column.

3. The apparatus of claim 1 further including a means for providing an inert gas to the interior of said container.

4. The apparatus of claim 1 wherein said inert gas is nitrogen.

5. The apparatus of claim 2 wherein said condenser is water-cooled.

6. The apparatus of claim 1 wherein said corrosion probes are maintained in position with glass hooks.

7. The apparatus of claim 1 wherein said given temperature of said liquid is determined with a thermocouple.

8. The apparatus of claim 1 wherein said vacuum pump is a mechanical pump.

9. The apparatus of claim 1 wherein said apparatus is used to evaluate corrosion inhibitors.

* * * * *